United States Patent
Leuchs et al.

(10) Patent No.: US 11,193,112 B2
(45) Date of Patent: Dec. 7, 2021

(54) SCALABLE PROCESS FOR ONCOLYTIC RAT PARVOVIRUS H-1 PRODUCTION AND PURIFICATION BASED ON ISOELECTRIC POINT-BASED ELIMINATION OF EMPTY PARTICLES

(71) Applicant: Deutsches Krebsforschungszentrum, Heidelberg (DE)

(72) Inventors: Barbara Leuchs, Heidelberg (DE); Jean Rommelaere, Heidelberg (DE); Veronika Frehtman, Heidelberg (DE); Markus Riese, Leinefelde-Worbis (DE)

(73) Assignee: DEUTSCHES KREBSFORSCHUNGSZENTRUM, Heidelberg (DE)

( * ) Notice: Subject to any disclaimer, the term of this patent is extended or adjusted under 35 U.S.C. 154(b) by 0 days.

(21) Appl. No.: 16/400,851

(22) Filed: May 1, 2019

(65) Prior Publication Data

US 2019/0256823 A1  Aug. 22, 2019

Related U.S. Application Data

(63) Continuation of application No. PCT/EP2017/073639, filed on Sep. 19, 2017.

(30) Foreign Application Priority Data

Nov. 9, 2016 (EP) .................................... 16198026

(51) Int. Cl.
*C12N 7/02* (2006.01)
*C12N 7/00* (2006.01)

(52) U.S. Cl.
CPC ...... *C12N 7/00* (2013.01); *C12N 2750/14351* (2013.01)

(58) Field of Classification Search
None
See application file for complete search history.

(56) References Cited

U.S. PATENT DOCUMENTS

2002/0127582 A1* 9/2002 Atkinson ............. C07D 409/14
435/6.11
2008/0299545 A1* 12/2008 Zhang ...................... C12N 7/00
435/5

(Continued)

FOREIGN PATENT DOCUMENTS

WO  2011094198 A1  8/2011
WO  2011/138053 A2  11/2011

OTHER PUBLICATIONS

GE Healthcare, "VisipaqueTM (Iodixanol) Injection," found at https://www.gehealthcare.com/en-GB/products/contrast-media/visipaque (Year: 2020).*

(Continued)

*Primary Examiner* — M Franco G Salvoza
(74) *Attorney, Agent, or Firm* — Perkins Coie LLP; Viola T. Kung

(57) ABSTRACT

The present invention provides a reproducible, effective and scalable process for the purification of (infectious) parvovirus H-1 particles. The purification process allows the separation of empty particles from particles containing a full genome and is compatible with large-scale H-1PV production for clinical applications.

7 Claims, 8 Drawing Sheets

(56) References Cited

U.S. PATENT DOCUMENTS

| | | | | |
|---|---|---|---|---|
| 2010/0098725 | A1* | 4/2010 | Liu | A61P 31/16 |
| | | | | 424/209.1 |
| 2011/0011742 | A1* | 1/2011 | Mathers | C07K 1/26 |
| | | | | 204/462 |
| 2013/0189265 | A1* | 7/2013 | Salome | A61P 35/00 |
| | | | | 424/139.1 |
| 2015/0299668 | A1* | 10/2015 | Yanagida | C12N 7/00 |
| | | | | 435/239 |
| 2019/0382733 | A1* | 12/2019 | Brument | C12Y 301/04035 |

OTHER PUBLICATIONS

Geletneky et al., "Bioavailability, Biodistribution, and CNS Toxicity of Clinical-Grade Parvovirus H1 after Intravenous and Intracerebral Injection in Rats," Comp Med. 65(1): 36-45 (Year: 2015).*

Sujata Halder, et al., "Production, purification, crystallization and structure determination of H-1 Parvovirus", Acta Crystallographica Section F Structural Biology and Crystallization Communications vol. 264, No. 12, Dec. 1, 2012, pp. 1571-1576.

Guy Ungerechts, et al., "Moving oncolytic viruses into the clinic: clinical-grade production, purification, and characterization of diverse oncolytic viruses", Molecular Therapy—Methods & Clinical Development, vol. 3, Jan. 1, 2016, p. 16018.

Barbara Leuchs, et al., "Standardized large-scale H-1PV production process with efficient quality and quantity monitoring", Journal of Virological Methods vol. 229, Dec. 2, 2015, pp. 48-59.

International Search Report dated Nov. 9, 2017 issued in PCT/EP2017/073639.

Bartel, M.A et al. "Directed evolution of novel adeno-associated viruses for therapeutic gene delivery" Gene Therapy, 2012, vol. 19, pp. 694-700.

Qu, G et al. "Separation of adeno-associated virus type 2 empty particles from genome containing vectors by anion-exchange col. chromatography" Journal of Virological Methods, 2007, vol. 140, pp. 183-192.

Urabe, M et al. "Removal of Empty Capsids from Type 1 Adeno-Associated Virus Vector Stocks by Anion-Exchange Chromatography Potentiates Transgene Expression" Molecular Therapy, 2006, vol. 13, No. 4, pp. 823-828.

* cited by examiner

SCALABLE PROCESS FOR ONCOLYTIC RAT PARVOVIRUS H-1 PRODUCTION AND PURIFICATION BASED ON ISOELECTRIC POINT-BASED ELIMINATION OF EMPTY PARTICLES

This application is a continuation of PCT/EP2017/073639, filed Sep. 19, 2017; which claims the priority of EP16198026.3, filed Nov. 9, 2016. The contents of the above-identified applications are incorporated herein by reference in their entirety.

The present invention provides a reproducible, effective and scalable process for the production and purification of (infectious) parvovirus H-1 particles. The purification process allows the separation of empty particles from particles containing a full genome and is compatible with large-scale H-1PV production for clinical applications.

H-1PV belongs to the genus *Protoparvovirus* within the Parvovirinae subfamily of Parvoviridae (Cotmore et al., 2014). It consists of a non-enveloped icosahedral capsid 25 nm in diameter and contains a single-stranded DNA genome about 5 kb long, encoding non-structural proteins—notably NS1 (83 kDa) and NS2 (25 kDa)—and the capsid proteins VP1 (81 kDa) and VP2 (65 kDa). Another capsid protein, VP3 (63 kDa), is generated by post-translational cleavage of VP2 (Faisst et al., 1995; Halder et al., 2012; Hanson and Rhode, 1991; Toolan et al., 1960). Protoparvoviruses replicate in a S-phase-dependent fashion and undergo a lytic cycle after infection of permissive cells (Burnett et al., 2006). While the natural host of H-1PV is the rat, this virus has recently raised much interest because it replicates preferentially in transformed cells, including a number of human tumor cells. The virus thus has oncolytic and oncosuppressive properties that have been demonstrated in various cell cultures and animal models (Nuesch et al., 2012; Rommelaere et al., 2010). In xenograft models, H-1PV has been shown to suppress a number of human tumors, including cervical tumors (Faisst et al., 1998; Li et al., 2013), pancreatic tumors (Angelova et al., 2009b; Grekova et al., 2011), mammary carcinomas (Dupressoir et al., 1989), gliomas (Geletneky et al., 2010; Kiprianova et al., 2011), and lymphomas (Angelova et al., 2009a). In addition, H-1PV has been shown to be successful in eliminating cancer stem cells (EP 2 404 609 A1). On the basis of these preclinical proofs of concept, a first clinical trial (phase I/IIa) of H-1PV was launched in 2011, for patients with recurrent glioblastoma multiforme (Geletneky et al., 2012).

To test and eventually exploit the therapeutic potential of H-1PV, it is necessary to develop an efficient, simple, and reproducible virus production and purification process. Purification methods have been published for small-scale production by cesium chloride (Halder et al., 2012; Paradiso, 1981) or Iodixanol (Wrzesinski et al., 2003; Zolotukhin et al., 1999) density gradient centrifugation.

Oncolytic protoparvovirus research has reached the stage of translation into clinical practice, with a first phase I/IIa study of H-1PV in patients with recurrent resectable malignant glioma (Geletneky et al., 2012).

At the moment a second phase I/II clinical trial has been initiated in patients with inoperable metastatic pancreatic cancer (ClinicalTrials.gov Identifier: NCT02653313; manuscript in preparation).

For these trials the H-1PV GMP batches were purified by density gradient centrifugation (Leuchs et al., 2016; Ungerechts et al., 2016), however, this method is limited in scale and the separation of empty particles from particles containing a full genome is not satisfactory. Furthermore, purified H-1PV has ultimately to be formulated into Visipaque (48% Iodixanol in Ringer solution), where the virus has known stability and which is also an X-ray contrast reagent for drug visualization in the human body.

Thus, the technical problem underlying the present invention is to provide a scalable purification process that allows the separation of empty particles from particles containing a full genome.

The solution of said technical problem is achieved by providing the embodiments characterized in the claims.

To satisfy these needs the inventors have developed a simple, scalable high-grade purification method for H-1PV. Empty particles are an undesirable by-product of H-1PV production, liable to cause an immune response without efficacy (Gao et al., 2014). Although ultracentrifugation-based methods have been used successfully to eliminate empty particles (Halder et al., 2012; Leuchs et al., 2016), these procedures are not really scalable, they are only semi-sterile, and fractionation is not well controllable. This explains why it was urgent to develop new purification approaches suitable for upscaling.

During the experiments resulting in the present invention major innovations for large-scale virus production, with elimination of unwanted contaminants through improved virus batch clarification and infectious particle purification were introduced. The inventors focused on developing standardized purification procedures as a basis for exploiting H-1PV both pre-clinically and in clinical trials for anticancer virotherapy.

Thus, the present application concerns a method for producing full active H-1 parvovirus particles, said method comprising:
 (a) providing the producer cell line NB-324K;
 (b) growing the cell line under suitable conditions and infecting the cells at a cell density from 2.0 to $5.0 \times 10^4$ cells/cm$^2$ with the parvovirus at a MCI of 0.5 to $2 \times 10^{-2}$ PFU/cells;
 (c) harvesting the cells 2 to 6 days post-infection and obtaining a cell pellet by centrifugation;
 (d) subjecting the resuspended cell pellet to a mechanical, physical or chemical cell lysis method for obtaining a parvovirus containing cell lysate;
 (e) sonicating the cell lysate and subjecting it to DNAse treatment;
 (f) clarifying the DNAse-treated parvovirus harvest by filtration; and
 (g) anion exchange chromatography to eliminate empty particles and most impurities;
 (h) buffer exchange and concentration through a desalting column or by a tangential flow filtration;
 (i) final formulation in Visipaque/Ringer solution.

The invention is further described in connection with the Figures which show:

Figure 1:
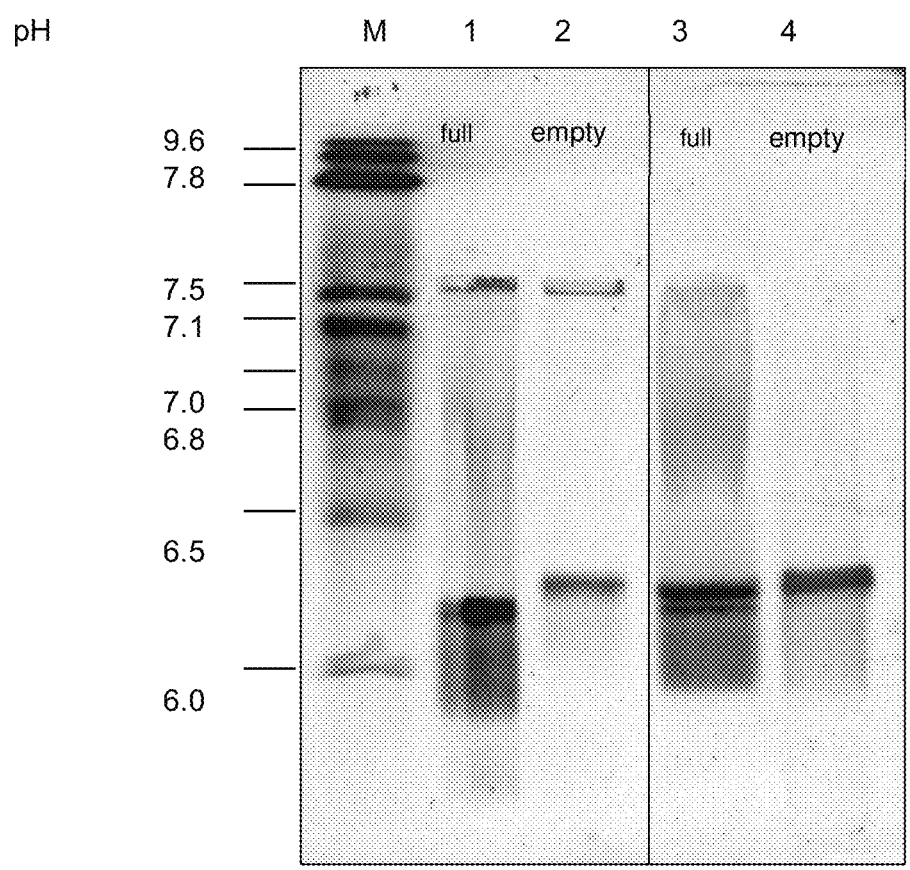
FIG. 1: Determination of the isoelectric points of H-1PV wt empty and full capsids by isoelectric focusing.

Two independently purified batches of empty or full capsids were loaded on the 0.9% agarose gel and focused in the electric field according to their respective pI values. The bands were visualized by silver staining. M: Biorad markers pH 4.45-9.6, lane 1: full particles from batch 1, lane 2: empty particles from batch 1, lane 3: full particles from batch 2, lane 4: empty particles from batch 2

Figure 2A:
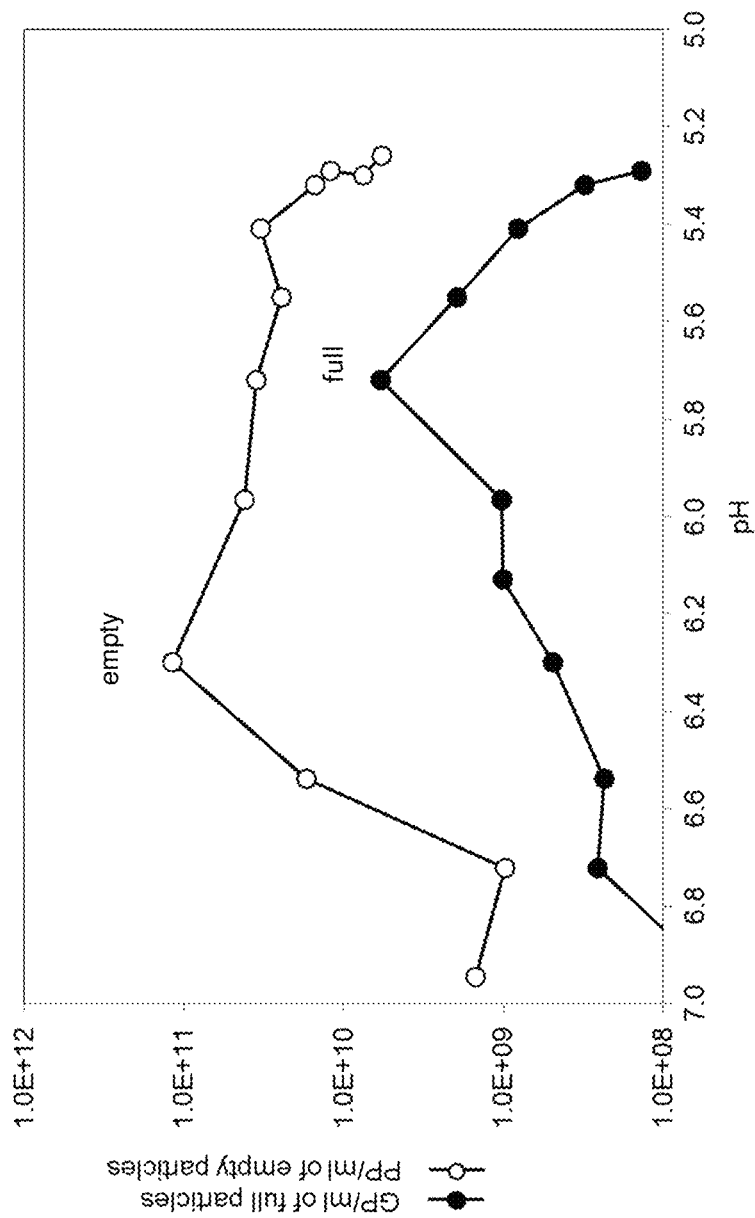
Figure 2B:
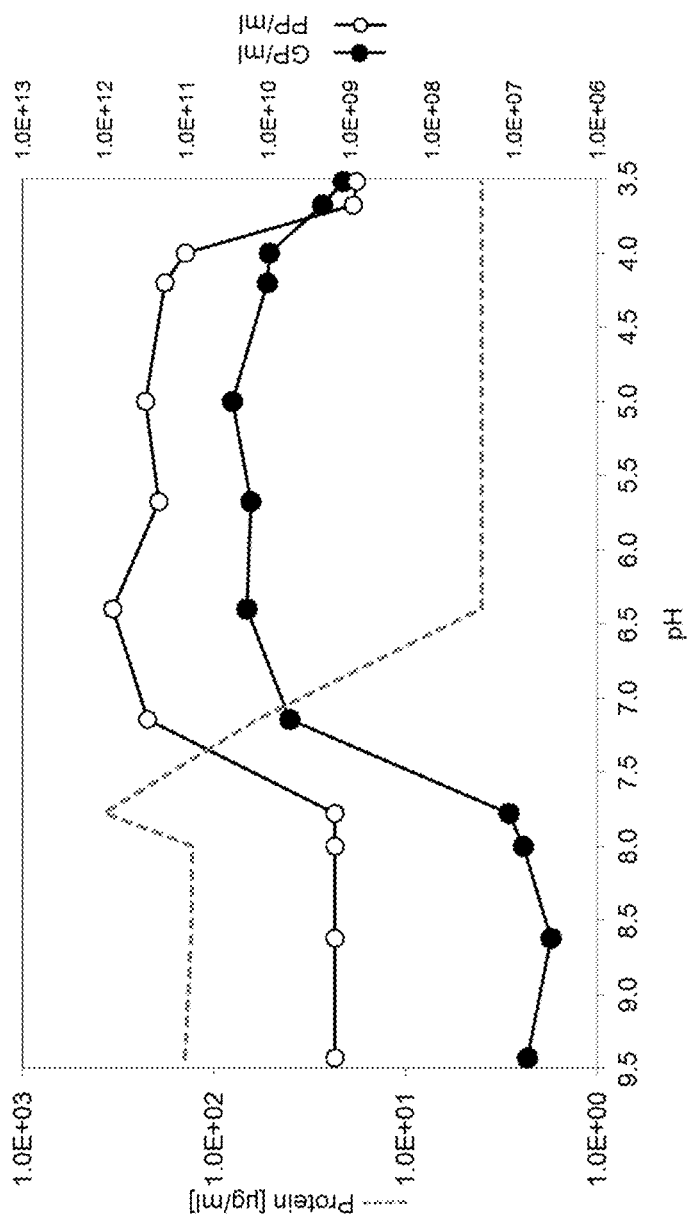

FIG. 2 *a*: pI profiles of empty and full H-1PV capsids obtained by chromatofocusing with a Mono P 5/50 column.

Two independently purified batches of empty or full capsids were loaded on Mono P 5/50 column and eluted according to their respective pI values. The fractions were analyzed for genome-containing particles (GP) and physical particles (PP).

The isoelectric point of empty capsid particles is at pH 6.3, as depicted by the physical particle peak and as evidenced by the PP-to-GP ratio (not shown); ratio ~900 at the pH corresponding to the PP peak. The Isoelectric point of full capsid particles was around pH 6.1-5.6. The PP-to-GP ratio (not shown) was near 1 in this pH range.

FIG. 2 b: pI profiles of empty and full H-1PV capsids and impurities obtained by chromatofocusing with a Mono P 5/50 column.

Unpurified batch was loaded on Mono P 5/50 column and eluted with pH gradient 9.5 to 3.5. The fractions were analyzed for genome-containing particles (GP), physical particles (PP) and protein content (protein impurities).

The impurities in the clarified cell lysate (host cell proteins, FBS) showed isoelectric points between pH 9.5 and 7.0, eluting from the Mono P column before pH 7.0.

FIG. 3 a: Optimal buffer and salt conditions for DEAE chromatography Pre-purified empty and full H-1PV particles in 50 mM Tris-HCl, pH 8.7 were applied to the DEAE column and eluted with a continuous 0-0.5M NaCl gradient. The elution profile shows the elution of empty capsid particles in fraction 8 (first UV absorbance peak) with 0.15 M NaCl (conductivity: 22 mS). The second UV absorbance peak, starting at fraction 11, shows desorption of full capsid particles at 0.2-0.25 M NaCl (conductivity: 29-32 mS). Physical particles (PP) and genome-containing particles (GP) were quantitated.

FIG. 3 b: Optimal buffer and salt conditions for DEAE chromatography

Clarified cell lysate was diluted in 50 mM Tris-HCl, pH 8.7 containing 0.15 M NaCl and applied to the DEAE column. Empty particles were recovered in the flow through and in the 0.15 M wash (first UV absorbance peak). Upon elution with a 0.15-0.4 M NaCl gradient, full particles eluted near 0.25 M NaCl (second UV absorbance peak). Physical particles (PP) and genome-containing particles (GP) were quantitated.

Figure 4:
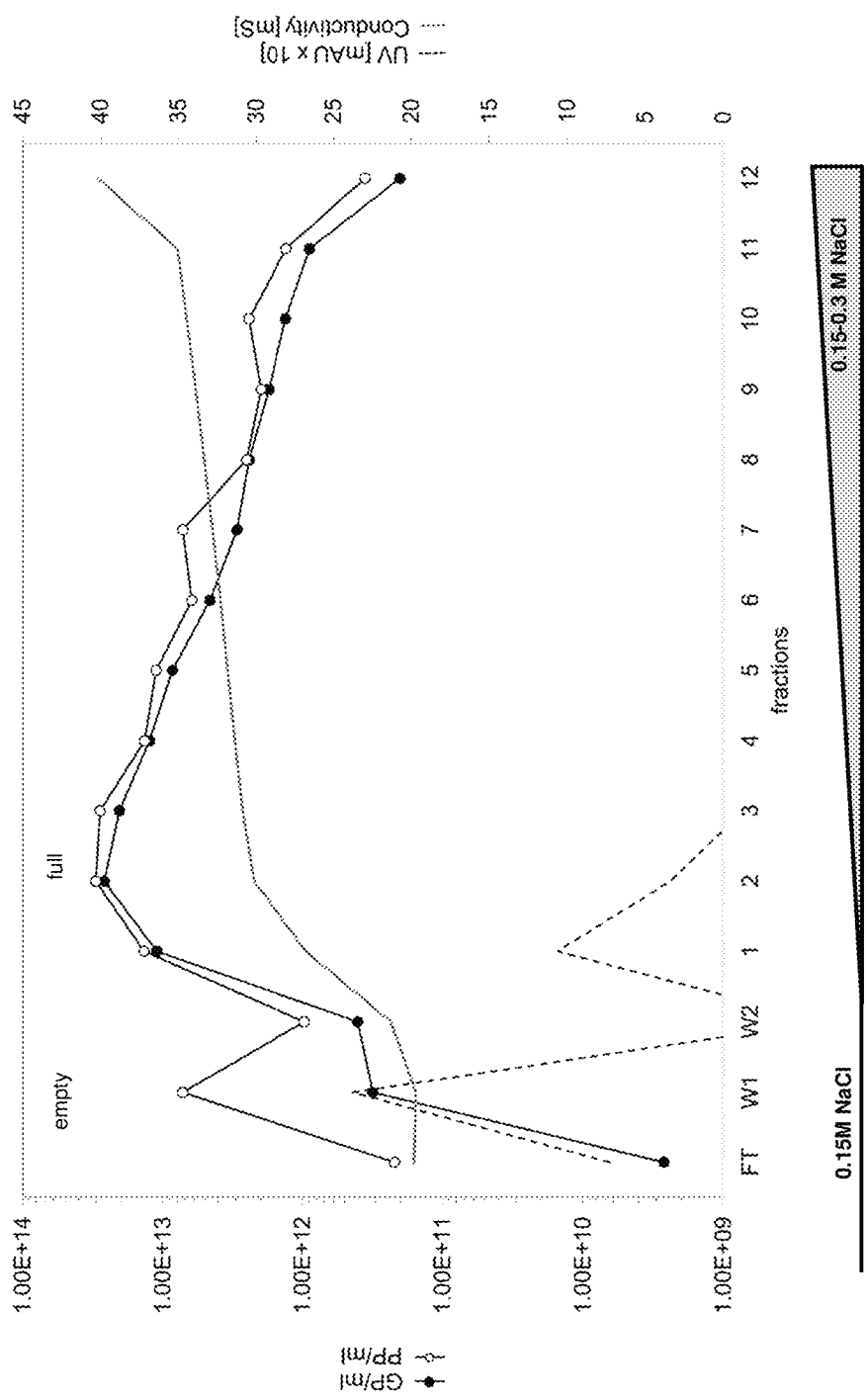

FIG. 4: Large-scale chromatography of a 2.3E8 cell harvest (corresponding to one 10-layer Cellstack®, reproduced 5 times) When clarified cell lysate diluted in 50 mM Tris-HCl pH 8.7 containing 0.15 M NaCl was loaded onto the 8 ml DEAE column, empty capsids eluted in the flow through and wash (first UV peak). Full capsids eluted in fractions 1-5 at NaCl concentration 0.25 M during elution with a continuous 0.15-0.3 M NaCl gradient (second UV peak, PP/GP ratio ~1).

Figure 5:
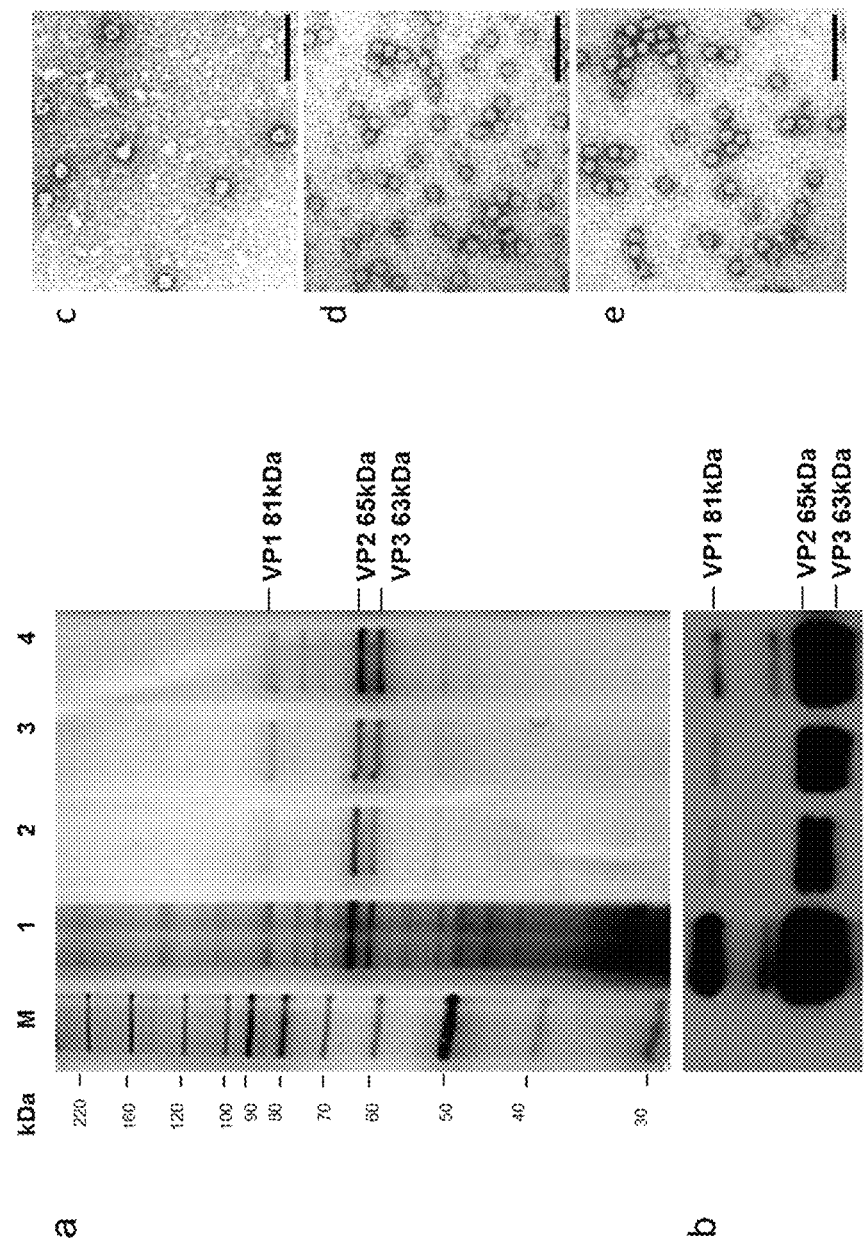

FIG. 5: Protein composition and electron microscope images of virus batches before and after the downstream process Panels a,b: Protein extracts of virus samples (1.0E10 PP) were analysed by SDS-PAGE and revealed by (a) silver staining or (b) immunblotting with αVP antibodies. M: markers constituting the BenchMark™ Protein Ladder, lane 1: virus harvest, lane 2: IOD-PBS—VIS-Ringer, line 3: DEAE—Vivaspin™—final formulation line 4: DEAE—HiTrap—final formulation.

Panels c,d,e: Electron micrographs showing clarified cell lysate (c), IOD-PBS—VIS-Ringer (d), DEAE—final formulation (e). Scale bar is 100 nm.

Figure 6:
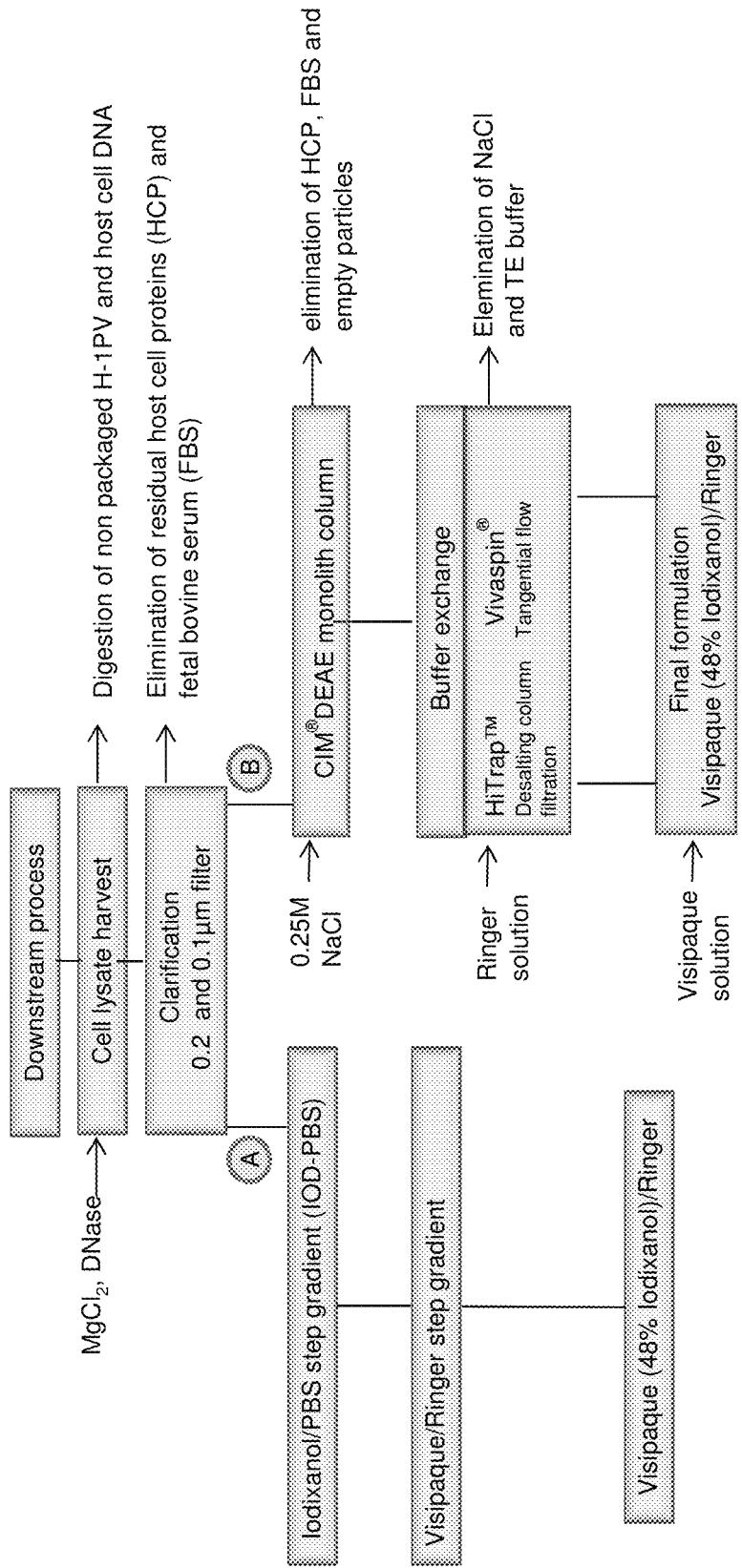

FIG. 6: Flow diagram of H-1PV downstream purification methods, comparing known IOD-PBS—VIS-Ringer gradient purification (A) with DEAE-final formulation methods (B)

The adopted production process of the present invention, which involves culturing and infecting NB-324K human newborn kidney cells transformed with simian virus 40 (SV40) (Tattersall and Bratton, 1983) in a conventional collection system (e.g. 10-layer CellSTACK® (CS) chambers; preferred yield: $1 \times 10^3$ infectious units per infected cell), is simple, scalable, and reproducible. The final downstream process of the present invention, which achieves the target virus titer of 1E10 PFU/ml, involves the following steps: (1) DNase treatment to eliminate host cell DNA; (2) Clarification (e.g. 0.2 µm followed by 0.1 µm filtration steps); (3) anion exchange chromatography to eliminate empty particles and most impurities; (4) passing the eluate of step (3) through a desalting column or a tangential flow filtration for buffer exchange and concentration; (5) final formulation in Visipaque/Ringer solution.

In detail, the present invention relates to a method for producing full active H-1 parvovirus particles, said method comprising:

(a) providing the producer cell line NB-324K;

(b) growing the cell line under suitable conditions and infecting the cells at a cell density from 2.0 to $5.0 \times 10^4$ cells/cm$^2$ with the parvovirus at a MOI of 0.5 to $2 \times 10^{-2}$ PFU/cells;

(c) harvesting the cells 2 to 6 days post-infection and obtaining a cell pellet by centrifugation;

(d) subjecting the resuspended cell pellet to a mechanical, physical or chemical cell lysis method for obtaining a parvovirus containing cell lysate;

(e) sonicating the cell lysate and subjecting it to DNAse treatment;

(f) clarifying the DNAse-treated parvovirus harvest by filtration (e.g. 0.2 µm followed by 0.1 µm filtration steps);

(g) anion exchange chromatography to eliminate empty particles and most impurities;

(h) buffer exchange and concentration through a desalting column or by tangential flow filtration;

(i) final formulation in Visipaque/Ringer solution.

The process of the present invention is shown in the flow diagram of FIG. 6 to which reference is made.

(A) Reproducible, Standardized, Large-Scale H-1PV Production

A virus yield of $2 \times 10^{11}$ PFU with a concentration of $1 \times 10^{10}$ PFU/ml, compatible with preclinical and clinical usage, was achieved with a single 10-layer CS chamber. This yield corresponds to a productivity of about $1 \times 10^3$ infectious particles per infected cell. The 10-layer system provides approximately the same attachment surface as a 100×10 cm cell culture dish (Halder et al., 2012). Efficient production was possible due to the good condition of the producer cells (NB-324K), with a viability over 95%, a passage number below 20, no *mycoplasma* contamination (Multiplexion, Germany), and the consistent quality of the FBS.

A simple and efficient way to achieve up-scaling was to use CS chambers, giving recoveries of up to $1 \times 10^{12}$ PFU from five 10-layer chambers. Further up-scaling would be possible with 40-layer chambers, although their handling of shaking and gassing is more cumbersome. Further up-scaling with adherent cells would involve the use of carriers, as described for vaccine production (Rajendran et al., 2014). An attractive alternative would be to use suspension cell cultures in wave reactors, as described for mink enteritis PV vaccine production (Hundt et al., 2007).

For optimum results, the producer cell line NB-324K is characterized by (i) a viability of at least 95%, (ii) a passage number below 20 (iii) lack of mycoplasma contamination, and (iv) lack of SV 40 production.

The person skilled in the art knows common conditions for growing the producer cell line and for infecting the cells with the parvovirus. Usually, the cells are cultured at 37° C., e.g., in minimal essential medium with heat-inactivated fetal bovine serum (e.g. FBS 5%) in a 5% $CO_2$ atmosphere. Preferably, the medium should be supplemented with penicillin, streptomycin and L-glutamine.

In a preferred embodiment of the present invention, the cell density of step (b) is from 3.0 to $4.0 \times 10^4$ cells/cm$^2$.

In a further preferred embodiment of the method of the present invention, virus production is performed in a single use cell culture system, preferably a 10-layer cell culture chamber, e.g. CellSTACK® (CS) chamber. Further upscaling may be achieved with a 40-layer CS chamber or a carrier system.

Preferably, for harvesting, the culture medium is aspirated and infected cells are treated with a suitable buffer and/or enzyme e.g. PBS-EDTA or Trypsin. The medium supernatant and detached cells are centrifuged for obtaining a cell pellet, preferably at 5,000×g, preferably for about 5 min. The person skilled in the art knows suitable mechanical, chemical or physical methods for releasing the parvovirus from the producer cells. Preferably, this can be done by freeze/thaw cycles, ultrasound treatment and/or Triton® 5100 treatment. The person skilled in the art also knows suitable methods for sonicating the cells and subsequent DNAse treatment. E.g., the cells can be sonicated at 30 to 70 W for a sufficient time and DNAse-treatment is carried out with 20-80 U/ml DNAse, usually at 37° C. for 10 to 50 min.

(B) Efficient Purification and Concentration of H-1PV Preparations

Unprocessed virus harvests contained full, empty, and intermediate-density particles, and were contaminated by both viral and host-cell DNA and proteins. They were first DNAse treated and then clarified through a filter (e.g. filtration through a 0.2 μm filter followed by filtration through a 0.1 μm filter). This resulted in elimination of 37% of the host-cell DNA and unpackaged viral DNA and of 24% of the total protein. Residual fragments of host-cell DNA proved to be smaller than 62 bp.

(C) Chromatographic Purification

As a basis for chromatographic purification, the inventors first determined the pI values of (a) empty and (b) full particles: (a) 6.3 and (b) 6.1 to 5.8. Isoelectric focusing and chromatofocusing gave similar results. For full particles, only a pI range could be obtained due to possible defective interfering virus particles (Faust and Ward, 1979). Knowledge of the isoelectric points of empty and full H-1PV was essential to develop the purification procedure and have implications for virus interactions, stability, production, and in vitro studies.

The inventors have tested the ability of different chromatographic systems to eliminate empty particles and impurities. Binding studies with H-1PV have demonstrated that the virus binds to and elutes from both cation and anion exchangers, but best recoveries were achieved with AEX chromatography and elution at pH 8.7. The inventors were also able to purify H-1PV on a strong anion exchange column (QA), with similar full particle recovery. Both systems were comparable in terms of recovery and protein impurity elimination. In a particular preferred embodiment DEAE chromatography is used. Likewise, as sodium chloride, sodium acetate, and ammonium acetate in the eluent gave rise to similar resolution of the peaks corresponding to empty and full capsids, sodium chloride is preferred for H-1PV purification because H-1PV is stable in this salt and because NaCl is present in the final formulation.

The fact that the pI difference between full and empty particles is at least 0.1 pH unit has enabled the inventors to develop a purification method which is based in one preferred embodiment on a DEAE column chromatography. In the present invention it has been shown that about 65% of the empty particles and about 67% of the main impurities can already be eliminated in the flow through with 0.1-0.2 M NaCl, preferably 0.15 M NaCl, and that about 50% of the full infectious virus particles can be eluted with 0.25-0.4 M salt, preferably 0.3 M salt. Thanks to the high stability of H-1PV, the purification can be performed at about room temperature (preferred operating temperature: 29±5° C.)

With the present method and conditions, the H-1PV elution profile could not be reproduced with the closely related protoparvovirus minute virus of mice (MVM) (data not shown), and empty MVM particles could not be separated from full ones.

The method as developed here is thus specific to H-1PV.

Although the present method offers an H-1PV yield of nearly 50% from the clarified cell lysate, one should note that the medium supernatant of the upstream process is still routinely discarded, amounting to a 30% loss (B. Leuchs et al., 2016). To demonstrate proof of concept and to test the ability of the inventive method to purify and concentrate H-1PV, clarified medium supernatant from routine production (corresponding to 1/10 of a 10-layer CS production) was purified as described here. After DEAE purification, total PFU recovery was about 50%, as observed with cell lysate, but the impurity content of H-1PV purified from culture medium supernatant was still high. Therefore, a second round of DEAE purification was performed, yielding ~20% total PFU recovery in a fiftieth of the initial volume. Over 99.7% of the protein impurities were eliminated after the second DEAE purification step, so that the protein content was the same as for purified cell lysate (data not shown).

As compared to Iodixanol-based ultracentrifugation (PCT/EP 2016/0001066) use of this novel purification strategy which involves anion exchange chromatography, preferably monolith-based DEAE anion exchange chromatography, significantly improves recovery and specific activity, leading to an optimal PP-to-GP ratio and significant elimination of empty particles (p values 0.05). The performance of the new method is similar to that of the ultracentrifugation-based CsCl density gradient method, in terms of the PP-to-GP ratio and PFU/mg protein (Leuchs et al., 2016). The virus titer of 1E10 PFU/ml is optimal, because the virus particles start to aggregate at 1E11 PFU/ml (as attested by high variance of the titer), and because preparations with a virus titer lower 1E8 PFU/ml are unstable over the years. The overall recovery of 40% with the purification strategy of the present invention, however, is superior to those known before (IOD-PBS—VIS-Ringer gradient). In this regard reference is made to Table 2 below.

Upscaling for clinical applications is possible, with the larger CIM® DEAE monolith columns (BIA Separations, USA) commercially available up to 8 L. The CIM® monolith is a single homogeneous piece cast from methacrylate polymers containing flow through pores (1.3 μm). DEAE (diethylaminoethyl) is a weak anion exchanger with a charged diethylamino group which selectively binds molecules with a predominant negative charge. These could be loaded with a total of 5E14 PFU, (corresponding to one thousand 10-layer CSs). Monolithic columns do not lose resolution with scale-up, so there is no need for new characterization studies. CIM® DEAE monolith columns offer a high binding capacity with high flow rates and low pressure which could significantly reduce purification time and costs. Furthermore, these columns can be used as disposables or for multiple uses and as a single column or in multicolumn setups. As the limiting loading capacity of an 8 ml column is 20 mg BSA/ml and as the inventors loaded such a column with only ~15 mg total protein (from cell lysate corresponding to 2.3E8 cells totalling about 5E11 PFU), the column could be loaded with 10 times as much.

TABLE 1

Comparison of five individual chromatography batches

| batch | Depletion of protein impurities [%] | PP [%] | Elution of GP [%] | PFU recovery [%] |
|---|---|---|---|---|
| 1 | 100 | 26 | 93 | 45 |
| 2 | 72 | 53 | 74 | 55 |
| 3 | 52 | 71 | 73 | 28 |
| 4 | 47 | 100 | 64 | 60 |
| 5 | 64 | 77 | 58 | 58 |
| mean [n = 5] | 67 ± 21 | 65 ± 28 | 72 ± 13 | 49 ± 13 |

Means with standard deviations for 5 independent chromatography runs.

(D) Formulation of Purified H-1PV after the Preparative DEAE Column Including Buffer Exchange with Tangential Flow Filtration or Size Exclution Chromatography The H-1PV eluate from the DEAE column contained about 0.25 M NaCl. To eliminate salt and formulate into VISIPAQUE® (48% Iodixanol in Ringer), it was necessary to perform buffer exchange into Ringer solution (AlleMan Pharma GmbH, Reutlingen, Germany) followed by formulation in VISIPAQUE® (48% Iodixanol in Ringer).

For buffer exchange into Ringer solution, two approaches were used: On the one hand, a 5 ml HITRAP® desalting column (GE Healthcare Europe GmbH, Freiburg, Germany) was used with the ÄKTAprime system. HITRAP® utilizes cross-linked dextran for size exclusion chromatography. The column was equilibrated first with 5 column volumes (CV) of Ringer solution. Then the sample was injected into a 5 ml sample loop filled with Ringer solution, loaded onto the column, and eluted with two CV of Ringer solution. One milliliter fractions were collected and analyzed for genome-containing particles and physical particles.

On the other hand, 6 ml VIVASPIN® concentrators (a polyethersulfone membrane with 30 KDa cut off, Sartorius AG, Göttingen, Germany) were used. The membrane ultra-filtration system was first sterilized with 70% ethanol for 20 min, centrifuged at 3000×g, rinsed with 6 ml sterile water for injection use, centrifuged again, and allowed to dry under laminar flow. Samples with a starting volume of about 1 ml were pipetted into the concentrator, diluted 1:5 with Ringer solution, and centrifuged at 3000×g until the volume reached 1 ml. Samples with a starting volume of 2 ml or more were first concentrated to 1 ml and then diluted with Ringer solution. This was done three times so as to dilute the initial buffer 1:125 in Ringer solution. The last concentration step was carried out down to a sample volume of ~300 µl. The refraction index of the sample was then measured with a digital refractometer AR200 (Reichert, Inc., Depew, N.Y., USA) and had to be that of Ringer solution (1.3342±0.0002).

The samples in Ringer solution obtained by one of the above methods were mixed with VISIPAQUE® 320 (contains 65.2% Iodixanol; GE Healthcare Europe GmbH, Freiburg, Germany) to 48% Iodixanol final concentration. The refraction index of the sample was then measured and had to be that of a 48% VISIPAQUE® solution (1.41±0.005).

"Iodixanol" is a synonym for "VISIPAQUE®" (for human injection use) or "Iodixanolum" (research grade). The IUPAC name is 5-[acetyl-[3-[N-acetyl-3,5-bis(2,3-di-hydroxypropylcarbamoyl) 2,4,6,-triiodoanilino]2-hydroxy-propyl]amino]-1-N,3,N-bis(2,3-dihydroxypropyl)-2,4,6-triiodobenzene-1,3-dicarboxamide. The CAS number is 92339-11-2. VISIPAQUE® is also a well-known contrast agent for CT imaging.

For the final formulation, both buffer exchange methods were suitable, but use of the VIVASPIN® tangential flow filtration system to exchange the buffer and simultaneously concentrate the sample to the desired volume is preferred with negligible loss. Furthermore, the tangential flow filtration is easily upscalable by using the proven polyethersulfone membrane with a pore size of about 30 kDa.

Buffer exchange with the HITRAP® desalting column leads to sample dilution and thus to a lower infectious virus titer in the final formulation. Between the two buffer-exchange methods, there is a one-log infectious virus titer difference in the final formulation (3.5E10 and 3.0E9 PFU/ml for VIVASPIN® and HITRAP® desalting, respectively).

The results are summarized in Table 2:

TABLE 2

Comparison of H-1PV recovery and depletion of empty particles as well as protein impurities by chromatography- and density gradient ultracentrifugation-based downstream process from the same starting material

| | Mehod of purification | | |
|---|---|---|---|
| | IOD-PBS - VIS-Ringer gradient | DEAE - Vivaspin ® Final formulation | DEAE - HiTrap ™ |
| | Visipaque (48% Iodixanol)/ Ringer | Visipaque (48% Iodixanol)/ Ringer | Visipaque (48% Iodixanol)/ Ringer |
| PFU/ml | 3.7 ± 0.6E+10 | 3.5 ± 0.5E+10 | 3.0 ± 0.3E+09 |
| volume [ml] | 1.3 ± 0.5 | 4.4 ± 0.2 | 39.1 ± 9.3 |
| PFU/mg protein* | 2.1 ± 0.1E+11 | 6.8 ± 2.5E+11 | 2.3 ± 0.3E11 |
| Recovery PFU %* | 13.1 ± 1.6 | 41.3 ± 15.5 | 42.3 ± 2.9 |
| PP-to-GP ratio* | 2.8 ± 0.5 | 1.1 ± 0.3 | 1.2 ± 0.0 |
| Depletion of protein impurities % | 98.5 ± 0.1 | 98.3 ± 0.3 | 96.5 ± 0.5 |
| Depletion of empty particles %* | 85.0 ± 1.3 | 95.8 ± 5.9 | 97.8 ± 1.5 |

Means with standard deviations (n = 2) of infectious titer (PFU/ml), recovery of infectious particles*, specific activity* (PFU/mg protein), the PP to GP ratio*, and depletion of empty particles* and protein impurities. The p-value is ≤0.05 for the features marked with *. For p-value calculation two further IOD-PBS-Vis-Ringer density gradient purified batches were taken into account.

In summary, the present invention concerns a scalable process offering high purity and recovery. Taking advantage of the isoelectric point difference between full and empty particles, it eliminates most empty particles. Full particles have a significantly higher cationic charge than empty ones, with an isoelectric point of 5.8-6.2 versus 6.3 (as determined by isoelectric focusing and chromatofocusing). Thanks to this difference, infectious full particles can be separated from empty particles and most protein impurities by anion exchange chromatography, e.g. CIM® DEAE anion exchange chromatography: applying unpurified H-1PV to the column in about 0.15 M NaCl leaves the former on the column and the latter in the flow through. The full particles are then recovered by elution with about 0.25-0.30 M NaCl. The whole large-scale purification process involves filtration, single-step (DEAE) anion exchange chromatography, buffer exchange by cross-flow filtration, and final formulation in Visipaque/Ringer solution. It results in 98% contaminating protein removal and 96% empty particle elimination. The final infectious particle concentration reaches 3.5E10 PFU/ml, with a specific activity of 6.8 E11 PFU/mg protein. Overall recovery is over 40%. It will facilitate aseptic upscaling according to GMP guidelines for clinical applications.

The present invention illustrates this standardization effort. It describes methods to support preclinical research. Improvements at three steps of H-1PV stock preparation were achieved: (1) reproducible, standardized, large-scale virus production, (2) virus purification and concentration by alternative procedures, and (3) implementation of quality control criteria.

The following examples are intended to illustrate, but not to limit the invention. While such examples are typical of those that might be used, other methods known to those skilled in the art may alternatively be utilized.

EXAMPLE 1

Determination of H-1PV pI

Isoelectric Focusing

Full and empty viral capsid preparations (CsCl density gradient purified) as obtained with the method described by Leuchs et al., 2016 and in PCT/EP 2016/001066 were separated in the electric field on the basis of their different isoelectric points (pI values).

All materials used for isoelectric focusing were purchased from Serva Electrophoresis GmbH, Heidelberg, Germany. The 0.9% agarose gels were cast on GelBond film with added 2.5% Servalyt carrier ampholytes pH 5-8 forming a pH gradient in an electric field. Gel electrophoresis was performed with the electrophoresis power supply EPS 3500 XL (Amersham Pharmacia Biotech Europe GmbH, Freiburg im Breisgau, Germany) under laminar flow. The system was cooled to 10° C. and the cooling reagent Bayol F was applied to the ceramic cooling plate between the gel and the plate. Filter paper strips soaked in electrode solutions were applied between the gel and the electrodes to maintain a stable gradient. An acidic solution was used at the anode and a basic one at the cathode. A 10 µl sample was placed on the gel surface by means of a silicon applicator strip with sample holes, laid on the gel surface. Separation conditions were as follows: isoelectric focusing of the sample at 250V, 10 mA, 10 W for 10 min; 500V, 10 mA, 10 W for 20 min; 1000V, 10 mA, 10 W for 40 min. Fixation and silver staining were performed according to Willoughby and Lambert, 1983 (Willoughby and Lambert, 1983).

Chromatofocusing

Chromatofocusing is a protein separation technique in which proteins elute from the column according to their pI.

Chromatofocusing of empty and full capsid virus preparations (CsCl density gradient purified) was done at RT under laminar flow with a Mono P 5/50 column (GE Healthcare Europe GmbH, Freiburg, Germany) and an ÄKTAprime equipped with a 500 µL injection loop. Mono P is a weak anion exchanger charged with mixed quaternary and tertiary amines. The flow rate of the mobile phase was 0.7 ml/min. The absorbance was monitored at 280 nm. All buffers and the sample were filtered through 0.2 µm filters. The application buffer was 0.025 M triethanolamine (Sigma-Aldrich Chemie GmbH, Steinheim, Germany) adjusted to pH 8.3 (for full and empty preparations) or 9.5 (for unpurified cell lysate) with concentrated iminodiacetic acid (Santa Cruz Biotechnology, Dallas, USA). The elution buffer consisted of Polybuffer 96 and Polybuffer 74 (GE Healthcare Europe GmbH, Freiburg, Germany) diluted according the manual's instruction in water for injection use and the pH was adjusted to 5.0 (for full and empty preparations) or 3.5 (for unpurified cell lysate) with concentrated iminodiacetic acid. The descending linear pH gradients (pH 8 to 5 for full and empty particle preparations and pH 9.4 to 3.5 for unpurified cell lysate) were obtained according to Mono P 5/50 manufacturer's instructions. For this, the column was equilibrated with application buffer at a pH slightly above the highest pH required. The elution buffer (adjusted to the lowest pH required) was passed through the column to generate first a pre-gradient. This was followed by application of the sample diluted in application buffer. Further application of the elution buffer to the column resulted in a moving descending pH gradient. This elution procedure led to formation of a pH gradient from pH 8.0 to 5.0 or from 9.4 to 3.5 with a Δ pH of 0.1-0.3 between fractions. Fractions of 0.5 or 1 ml were collected and analyzed for GP and PP. The pH of the collected fractions was measured manually with a Mettler Toledo InLab Viscous Pro pH electrode.

Isoelectric Point of H-1PV and Process Impurities

In order to separate empty from full H-1PV wt viral particles, it was necessary to find an exploitable difference in their physical properties. Isoelectric focusing was performed on purified empty and full particle preparations to determine the respective isoelectric points of these particles. The results (FIG. 1) revealed a pI of 6.3 for empty particles and of 5.8-6.2 for full particles (with negligible contamination by empty capsids). To see if this pI difference might be exploited in purifying infectious virus (i.e. to eliminate empty particles and contaminating proteins), chromatofocusing was used. First, CsCl purified empty or full particle preparations were loaded onto a Mono P 5/50 column and eluted as described above. By this procedure (FIG. 2a), chromatofocusing identified a pI of 6.3 for empty particles (PP-to-GP ratio: ~869; data not shown) and of 6.1-5.8 for full particles (PP-to-GP ratio: ~1; data not shown), thus confirming the results obtained by isoelectric focusing. Furthermore, chromatofocusing was used to estimate the pI range of impurities (host cell proteins, FBS) present in the clarified cell lysate. A significant amount of impurities eluted from the Mono P column at basic pH (pI range 9.4 to 7). The PP-to-GP ratio was 43 at pH 6.4 versus 13 at near pH 5.7, in keeping with the pI values determined for empty and full particles.

EXAMPLE 2

Small-Scale Anion Exchange (AEX) Chromatography for Determining Optimal Buffer and Salt Conditions The isoelectric points of proteins correlate with the charge at which they bind to/elute from the chromatography column. As the salt concentration increases, proteins with the weakest ionic interactions elute from the column first. With knowledge of the pI values of empty and full H-1PV particles and of the impurities arising during production, it is possible to separate these entities by AEX chromatography: most protein impurities should elute first, followed by empty particles and finally, full particles.

As equilibration buffer for the AEX chromatography, 50 mM Tris-HCl pH 8.7 was chosen for its compatibility with virus harvest. For optimal binding, in theory, the pH of the buffer has to be at least 1-2 pH units above the pI of the protein (Fekete et al., 2015). At pH 8.7, the impurities should not bind, as they are weakly negatively charged, neutral, or even positively charged (pI between pH 9.5 and 7.0). Since the pI is 6.3 for H-1PV empty particles and 5.8-6.1 for full particles, the virus is negatively charged at pH 8.7. Preliminary studies performed with different ion exchange columns to determine binding and elution conditions (data not shown) demonstrated that a weak anion exchanger (DEAE) column is the best choice for H-1PV purification. A CIM® DEAE monolith column with a 1.3 µm pore size was chosen for the chromatographic studies because of its ability to accommodate large molecules specifically while maintaining good mechanical stability.

Figure 3A:
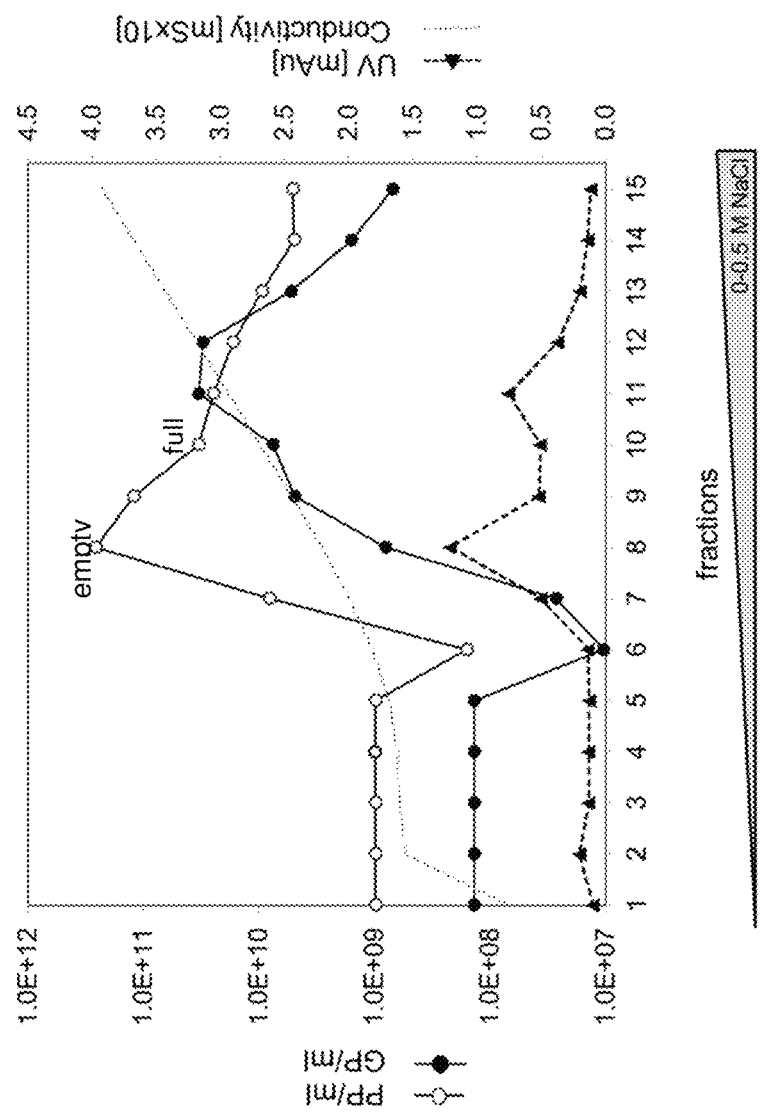

Sodium chloride, sodium acetate, and ammonium acetate were tested to determine the best salt for elution. A mixture of pre-purified empty and full particles was applied to a 0.34 ml CIM® DEAE monolith disk and eluted with a continuous 0-0.5 M gradient of the tested salt in 50 mM Tris-HCl pH 8.7. The peak fractions were analyzed for their PP and GP content. All elution profiles displayed two UV absorbance peaks: one corresponding to empty particles followed by one corresponding to full particles. As all the salts tested proved suitable for separating empty from full particles, it was decided to continue working with NaCl because H-1PV is stable in NaCl solution (data not shown) and because NaCl is present in the desired final Visipaque/Ringer formulation (0.053 M NaCl). When a continuous gradient of NaCl was applied (0-0.5 M NaCl in 50 mM Tris-HCl pH 8.7), the empty particles eluted at 0.13-0.15 M NaCl (PP-to-GP ratio: ~300) and full particles at 0.2-0.25 M NaCl (PP-to-GP ratio: ~1) (FIG. 3a). As these salt concentrations could not be measured directly, the corresponding conductivity values were also measured (18-22 mS for empty particles and over 25 mS for full particles) to ensure a reproducible purification process in further development experiments.

Figure 3B:
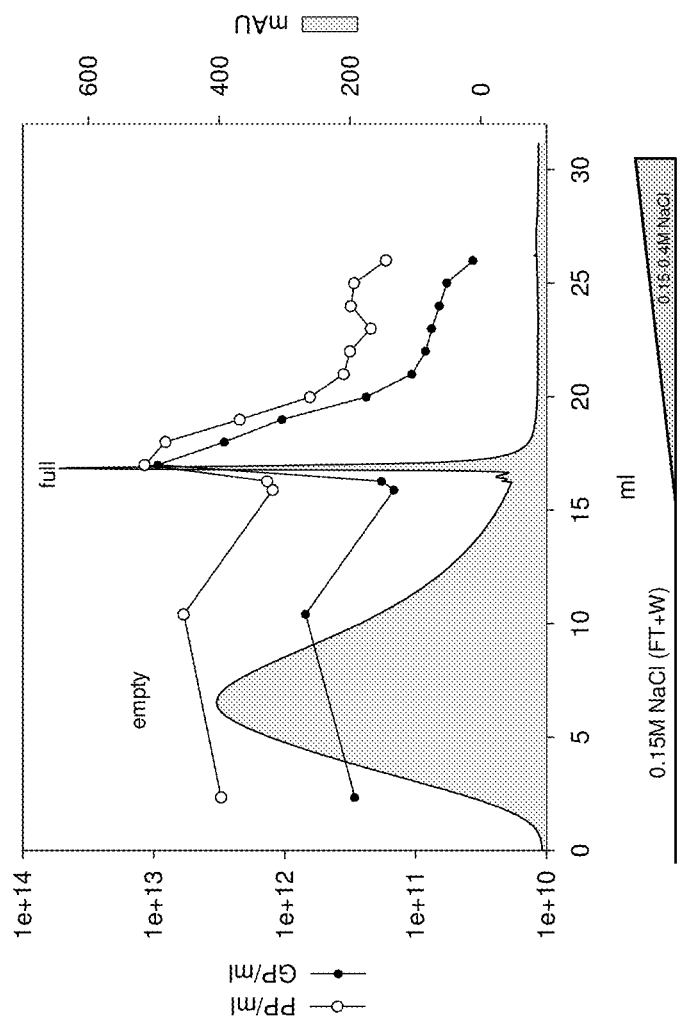

In a subsequent experiment, a small amount of clarified H-1PV harvest was prepared in 50 mM Tris-HCl pH 8.7 with 0.15 M NaCl and loaded onto the 0.34 ml CIM® DEAE monolith disk to allow flow through of empty particles as well as impurities and binding of full particles to the column. The disk was then eluted with a 0.15-0.4 M NaCl gradient. As shown in the chromatogram of FIG. 3b, about 70% of the empty particles and 60% of the protein impurities were eliminated in the flow through and wash (first UV peak), whereas about 60% of the full particles eluted near 0.25 M NaCl (second UV peak).

Reproduced Large-Scale Single Step AEX Chromatography

After determination of the optimal buffer and salt conditions, a large-scale purification was performed with clarified cell lysate from 2.3E8 cells (corresponding to the production of one 10-layer CS). Clarified cell lysate diluted in 50 mM Tris-HCl pH 8.7 containing 0.15 M NaCl was loaded onto an 8 ml CIM® DEAE monolith column and eluted with a continuous salt gradient (0.15-0.3 M NaCl in 50 mM Tris-HCl pH 8.7). As seen in FIG. 4, empty particles eluted in the flow through and wash (first UV peak) (PP-to-GP ratio near 50.0; 2.3E14 total PP). Full particles eluted at 0.2-0.25 M NaCl (conductivity: 26-31.8 mS, second UV peak). The virus concentration was approximately 1E13 GP/ml and 1E10 PFU/ml (data not shown) and the PP-to-GP ratio was about 1.

Chromatographic purification of clarified H-1PV cell lysate was reproduced for five individual batches. These experiments revealed elimination of 67±21% protein impurities and 65±28% empty particles, with recovery of 72±13% GP and 49±13% PFU (Table 1). The salt concentration required for full infectious particles was 0.2-0.25 M NaCl, with a conductivity of 25-31.8 mS. Taken together, these results show that for the final formulation, it should be possible, in the future, to collect only one fraction, corresponding to this conductivity range.

Buffer Exchange and Final Formulation after AEX Chromatography

For the final formulation in VISIPAQUE®/Ringer solution, the full particle eluate from the DEAE column had first to be buffer exchanged into Ringer solution and finally mixed with VISIPAQUE® to obtain a refraction index of 1.41±0.05, corresponding to 48% iodixanol. Two buffer exchange methods were tested: use of a HITRAP® desalting column and use of VIVASPIN® concentrators. Each method was applied twice. The results were compared with those obtained by the standard purification method (density gradient centrifugation in IOD-PBS followed by VIS-Ringer) applied to the same virus harvest batch. Table 2 summarizes the results. With the newly developed chromatographic purification method, a preparation containing only full particles was obtained (PP-to-GP ratio ~1). PFU recovery was at least twice as high (around 40%) as with the standard method, and the specific activity was similar (or even higher after VIVASPIN® cross-flow filtration). The infectious virus titer obtained either by the standard method or by DEAE chromatography with VIVASPIN® filtration was about 3E10 PFU/ml; after DEAE chromatography and HITRAP® desalting, it was 3E9 PFU/ml. The three methods reduced protein impurities with equal effectiveness (>96%), but chromatographic purification followed by either buffer exchange procedure eliminated empty particles more effectively (>95%) than the standard method (85%). Virus purity, as determined by SDS-PAGE with silver staining, was the same after all three procedures (FIG. 5). Electron micrographs of the preparations obtained by the novel strategy showed full particles predominantly, in contrast to standard preparations. The flow diagram in FIG. 6 summarizes the downstream process steps of all three methods. Quality control tests demonstrated that all final formulated batches were sterile.

EXAMPLE 3

Purified H-1PV Preparation (A) Producer Cell Line, H-1PV Virus Stock

NB-324K human newborn kidney cells transformed with simian virus 40 (SV40) (Tattersall and Bratton, 1983) were cultured at 37° C. in minimum essential medium (MEM, Sigma, Germany) with 5% heat-inactivated fetal bovine serum (FBS, Biowest, France) in a 5% $CO_2$ atmosphere. The medium was supplemented with 100 U/ml penicillin, 100 µg/ml streptomycin, and 2 mM L-glutamine (Life Technologies, Germany). For production, NB-324K cells propagated in 175-$cm^2$ Y-flasks (Nunc, Denmark) were seeded into a 10-layer CELLSTACK® culture chamber (Corning, Germany) with a 6,360 $cm^2$ growth area. Cell density and viability were measured by staining living cells with 0.4% trypan blue (Invitrogen, Germany). Cells were counted with a COUNTESS® Cell counter (Life Technologies, Germany). An in-house purified H-1PV virus stock was used to infect the cells.

(B) H-1PV Production

A 10-layer CELLSTACK® (CS) was chosen as a convenient single-use production system. For simultaneous cell seeding and infection, NB-324K cells were seeded at 3.6× $10^4$ cells/$cm^2$ into the 10-layer CS and infected immediately with H-1PV at a multiplicity of infection (MOI) of 0.01 plaque forming units (PFU) per cell. The pH during infection was 7.0±0.1. The infected cells were incubated for 4 days at 37° C. under 5% $CO_2$ until the cytopathic effect (CPE), measured as the percentage of dead and detached cells observed under a microscope, reached at least 30%. For non-simultaneous seeding and infection, NB-324K cells were seeded at $7.9 \times 10^3$ cells/cm² into a 10-layer CS and allowed to grow for three days, by which time they had reached a density of approximately $3.6 \times 10^4$ cells/cm², as measured on a control-flask culture. These anchored cells were then infected at a MOI of 0.01 PFU/cell and incubated for 4 days as described above. For harvesting, the medium was aspirated and infected cells were treated with PBS/1 mM EDTA. The medium supernatant and detached cells were centrifuged for 5 min at 5,000×g. The pellet was washed with PBS, resuspended in Tris/EDTA buffer (TRIZMA® hydrochloride; Sigma-Aldrich Co. St. Louis, USA) and subjected to three freeze/thaw cycles. After centrifugation for 5 min at 5,000×g, cell debris were discarded. The cell lysate was then sonicated at 48 W for 1 min in a Sonorex Super 10 P ultrasonic homogenizer (Bandelin, Germany) and treated with DNAse (50 U/ml, Sigma, Germany) for 30 min at 37° C.

For more details reference is made to Leuchs et al., 2016 and PCT/EP 2016/001066.

(C) H-1PV Purification

The DNase-treated virus harvest was clarified by filtration through a 0.2-μm Sartolab® P20 Plus filter and 0.1 μm Sartolab® P20 Plus filter (Sartorius, Germany)

(D) Small- and Large-Scale DEAE Anion Exchange Chromatography (AEX)

All chromatographic studies were performed with a 0.34 ml CIM® DEAE monolith disk or an 8 ml CIM® DEAE monolith column (1.3 μm pore size; Bia Separations, Ajdovscina, Slovenia) and ÄKTAprime (GE Healthcare Europe GmbH, Freiburg, Germany) at room temperature (RT) under laminar flow. The CIM® monolith is a single homogeneous piece cast from methacrylate polymers containing flow through pores. DEAE (diethylaminoethyl) is a weak anion exchanger with a charged diethylamino group which selectively binds molecules with a predominant negative charge. The flow rate of the mobile phase was 0.7 ml/min or 2 ml/min depending on the column size. Absorbance was monitored at 280 nm and is expressed in milli absorbance units (mAu). Conductivity is expressed in milliSiemens (mS). All buffers were filtered through 0.2 μm filters. The column was equilibrated with the application buffer prior to the start of each run, until constant conductivity and UV absorbance values were observed. Elution steps were followed by a high-salt wash with 1 M NaCl (Sigma-Aldrich Chemie GmbH, Steinheim, Germany). The application buffer was 50 mM Tris-HCl or 0.15 M NaCl in 50 mM Tris-HCl, adjusted to pH 8.7. The sample obtained in (C) above was diluted in application buffer and applied to the column. This was followed by a wash with application buffer until baseline UV absorbance was reached. Elution was performed with a continuous salt gradient from 0 to 0.5 M NaCl in 50 mM Tris-HCl pH 8.7 or from 0.15 M to 0.4 M (0.3 M for large-scale) NaCl in 50 mM Tris-HCl pH 8.7. One milliliter fractions were collected during the runs and analyzed for genome-containing particles (GP), physical particles (PP), and plaque forming units. Because plaque forming unit evaluation is a laborious cell-based method, it was done only in large-scale chromatographic experiments and for analysis of the final formulation, given the importance of the infectious virus titer in anticancer virotherapy.

(E) Formulation of Purified H-1PV after the Preparative DEAE Column

The H-1PV eluate from the DEAE column contained 0.25 M NaCl. To eliminate salt and formulate into Visipaque (48% Iodixanol in Ringer), it was necessary to perform buffer exchange into Ringer solution (AlleMan Pharma GmbH, Reutlingen, Germany) followed by formulation in Visipaque (48% Iodixanol in Ringer).

For buffer exchange into Ringer solution, two approaches were used:

On the one hand, a 5 ml HiTrap™ desalting column (GE Healthcare Europe GmbH, Freiburg, Germany) was used with the ÄKTAprime system. HiTrap™ utilizes cross-linked dextran for size exclusion chromatography. The column was equilibrated first with 5 column volumes (CV) of Ringer solution. Then the sample was injected into a 5 ml sample loop filled with Ringer solution, loaded onto the column, and eluted with two CV of Ringer solution. One milliliter fractions were collected and analyzed for genome-containing particles and physical particles. On the other hand, ml Vivaspin® concentrators (cut-off 30 kDa; Sartorius AG, Göttingen, Germany) were used. The membrane ultrafiltration system was first sterilized with 70% ethanol for 20 min, centrifuged at 3000×g, rinsed with 6 ml sterile water for injection use, centrifuged again, and allowed to dry under laminar flow. Samples with a starting volume of about 1 ml were pipetted into the concentrator, diluted 1:5 with Ringer solution, and centrifuged at 3000×g until the volume reached 1 ml. Samples with a starting volume of 2 ml or more were first concentrated to 1 ml and then diluted with Ringer solution. This was done three times so as to dilute the initial buffer 1:125 in Ringer solution. The last concentration step was carried out down to a sample volume of ~300 μl. The refraction index of the sample was then measured with a digital refractometer AR200 (Reichert, Inc., Depew, N.Y., USA) and had to be that of Ringer solution (1.3342±0.0002).

The samples in Ringer solution obtained by one of the above methods were mixed with VISIPAQUE® 320 (contains 65.2% Iodixanol; GE Healthcare Europe GmbH, Freiburg, Germany) to 48% Iodixanol final concentration. The refraction index of the sample was then measured and had to be that of a 48% VISIPAQUE® solution (1.41±0.005).

(F) Quantification and Qualification of H-1PV Batches

Virus quantification and characterization were done by plaque formation assay (for infectious particles), qPCR (for GP), H-1PV Capsid-ELISA (for PP), protein quantification and SDS-PAGE (silver staining), western blotting, and sterility assessment (see B. Leuchs et al., 2016 for method description).

Electron Microscopy

Electron microscopic analysis of the purified virus batches was performed according to Leuchs et al., 2016 with a few minor modifications. A pre-incubation step with 0.05% BSA solution for min was added before sample incubation as well as virus deactivation step with 0.1% glutaraldehyde for 5 min after sample incubation. Photos were taken with a Zeiss EM 900 transmission electron microscope (Carl Zeiss Microscopy GmbH, Jena, Germany) at 85,000× magnification.

LIST OF REFERENCES

Acikara, Ö., 2013. Ion-Exchange Chromatography and Its Applications, Column Chromatography, Dr. Dean Martin (Ed.), InTech, DOI: 10.5772/55744. Available from: www.intechopen.com/books/column-chromatography/ion-exchange-chromatography-and-its-applications Adamson-Small, L., Potter, M., Falk, D. J., Cleaver, B., Byrne, B. J. and Clement, N., 2016. A scalable method for the production of high-titer and high-quality adeno-associated type 9 vectors using the HSV platform. Mol Ther Methods Clin Dev 3, 16031.

Angelova, A. L., Aprahamian, M., Balboni, G., Delecluse, H. J., Feederle, R., Kiprianova, I., Grekova, S. P., Galabov, A. S., Witzens-Harig, M., Ho, A. D., Rommelaere, J. and Raykov, Z., 2009a. Oncolytic rat parvovirus H-1PV, a candidate for the treatment of human lymphoma: In vitro and in vivo studies. Molecular therapy; The journal of the American Society of Gene Therapy 17, 1164-72.

Angelova, A. L., Aprahamian, M., Grekova, S. P., Hajri, A., Leuchs, B., Giese, N. A., Dinsart, C., Herrmann, A., Balboni, G., Rommelaere, J. and Raykov, Z., 2009b. Improvement of Gemcitabine-Based Therapy of Pancreatic Carcinoma by Means of Oncolytic Parvovirus H-1PV. Clinical Cancer Research 15, 511-519.

Burnett, E., Cotmore, S. F. and Tattersall, P., 2006. Segregation of a single outboard left-end origin is essential for the viability of parvovirus minute virus of mice. J Virol 80, 10879-83.

Cotmore, S. F., Agbandje-McKenna, M., Chiorini, J. A., Mukha, D. V., Pintel, D. J., Qiu, J., Soderlund-Venermo, M., Tattersall, P., Tijssen, P., Gatherer, D. and Davison, A. J., 2014. The family Parvoviridae. Archives of virology 159, 1239-47.

Dupressoir, T., Vanacker, J. M., Cornelis, J. J., Duponchel, N. and Rommelaere, J., 1989. Inhibition by parvovirus H-1 of the formation of tumors in nude mice and colonies in vitro by transformed human mammary epithelial cells. Cancer research 49, 3203-8.

Faisst, S., Faisst, S. R., Dupressoir, T., Plaza, S., Pujol, A., Jauniaux, J. C., Rhode, S. L. and Rommelaere, J., 1995. Isolation of a Fully Infectious Variant of Parvovirus H-1 Supplanting the Standard Strain in Human-Cells. Journal of Virology 69, 4538-4543.

Faisst, S., Guittard, D., Benner, A., Cesbron, J. Y., Schlehofer, J. R., Rommelaere, J. and Dupressoir, T., 1998. Dose-dependent regression of HeLa cell-derived tumours in SCID mice after parvovirus H-1 infection. International journal of cancer. Journal international du cancer 75, 584-9.

Faust, E. A. and Ward, D. C., 1979. Incomplete genomes of the parvovirus minute virus of mice: selective conservation of genome termini, including the origin for DNA replication. J Virol 32, 276-92.

Fekete, S., Beck, A., Veuthey, J. L. and Guillarme, D., 2015. Ion-exchange chromatography for the characterization of biopharmaceuticals. J Pharm Biomed Anal 113, 43-55.

Gao, K., Mengxin, L., Li, Z., Qin, S., Jia, L., Shaoyong, L., Ran, H., Yu, Z., Gregory, H., Junzhi, W. and Guangping, G., 2014. Empty virions in AAV8 vector preparations reduce transduction efficiency and may cause total viral particle dose-limiting side effects. Molecular Therapy—Methods & Clinical Development 1, 20139.

Geletneky, K., Huesing, J., Rommelaere, J., Schlehofer, J. R., Leuchs, B., Dahm, M., Krebs, O., von Knebel Doeberitz, M., Huber, B. and Hajda, J., 2012. Phase I/IIa study of intratumoral/intracerebral or intravenous/intracerebral administration of Parvovirus H-1 (ParvOryx) in patients with progressive primary or recurrent glioblastoma multiforme: ParvOryx01 protocol. BMC cancer 12, 99.

Geletneky, K., Kiprianova, I., Ayache, A., Koch, R., Herrero, Y. C. M., Deleu, L., Sommer, C., Thomas, N., Rommelaere, J. and Schlehofer, J. R., 2010. Regression of advanced rat and human gliomas by local or systemic treatment with oncolytic parvovirus H-1 in rat models. Neuro-oncology 12, 804-14.

Grekova, S. P., Aprahamian, M., Daeffler, L., Leuchs, B., Angelova, A., Giese, T., Galabov, A., Heller, A., Giese, N. A., Rommelaere, J. and Raykov, Z., 2011. Interferon gamma improves the vaccination potential of oncolytic parvovirus H-1PV for the treatment of peritoneal carcinomatosis in pancreatic cancer. Cancer biology & therapy 12, 888-95.

Griffith, O. M., 2006. Practical Techniques for centrifugal separations. FiberLite, Piramon Technologies, Inc.

Halder, S., Nam, H. J., Govindasamy, L., Vogel, M., Dinsart, C., Salome, N., McKenna, R. and Agbandje-McKenna, M., 2012. Production, purification, crystallization and structure determination of H-1 Parvovirus. Acta crystallographica. Section F, Structural biology and crystallization communications 68, 1571-6.

Hanson, N. D. and Rhode, S. L., 3rd, 1991. Parvovirus NS1 stimulates P4 expression by interaction with the terminal repeats and through DNA amplification. J Virol 65, 4325-33.

Hundt, B., Best, C., Schlawin, N., Kassner, H., Genzel, Y. and Reichl, U., 2007. Establishment of a mink enteritis vaccine production process in stirred-tank reactor and Wave Bioreactor microcarrier culture in 1-10 L scale. Vaccine 25, 3987-95.

Kestler, J., Neeb, B., Struyf, S., Van Damme, J., Cotmore, S. F., D'Abramo, A., Tattersall, P., Rommelaere, J., Dinsart, C. and Cornelis, J. J., 1999. cis requirements for the efficient production of recombinant DNA vectors based on autonomous parvoviruses. Human Gene Therapy 10, 1619-1632.

Kiprianova, I., Thomas, N., Ayache, A., Fischer, M., Leuchs, B., Klein, M., Rommelaere, J. and Schlehofer, J. R., 2011. Regression of Glioma in Rat Models by Intranasal Application of Parvovirus H-1. Clinical Cancer Research 17, 5333-5342.

Kongsvik, J. R. and Toolan, H. W., 1972. Effect of proteolytic enzymes on the hemagglutinating property of the parvoviruses, H-1, H-3, and RV. Proceedings of the Society for Experimental Biology and Medicine. Society for Experimental Biology and Medicine 140, 140-4.

Kuck, D., Kern, A. and Kleinschmidt, J. A., 2007. Development of AAV serotype-specific ELISAs using novel monoclonal antibodies. J Virol Methods 140, 17-24.

Lacroix, J., Leuchs, B., Li, J., Hristov, G., Deubzer, H. E., Kulozik, A. E., Rommelaere, J., Schlehofer, J. R. and Witt, O., 2010. Parvovirus H1 selectively induces cytotoxic effects on human neuroblastoma cells. International journal of cancer. Journal international du cancer 127, 1230-9.

Leuchs, B., Roscher, M., Muller, M., Kurschner, K. and Rommelaere, J., 2016. Standardized large-scale H-1PV production process with efficient quality and quantity monitoring. J Virol Methods 229, 48-59.

Li, J., Bonifati, S., Hristov, G., Marttila, T., Valmary-Degano, S., Stanzel, S., Schnolzer, M., Mougin, C., Aprahamian, M., Grekova, S. P., Raykov, Z., Rommelaere, J. and Marchini, A., 2013. Synergistic combination of valproic acid and oncolytic parvovirus H-1PV as a potential therapy against cervical and pancreatic carcinomas. EMBO molecular medicine 5, 1537-55.

Malyala, P. and Singh, M., 2008. Endotoxin limits in formulations for preclinical research. Journal of pharmaceutical sciences 97, 2041-4.

Merten, O. W., Hebben, M. and Bovolenta, C., 2016. Production of lentiviral vectors. Mol Ther Methods Clin Dev 3, 16017.

Mihelic, Koloini, Podgornik and trancar, S., 2000. Dynamic Capacity Studies of CIM (Convective Interaction Media) R Monolithic Columns. J. High Resol. Chromatogr. 23 39-43.

Mihelic, I., Podgornik, A. and Koloini, T., 2003. Temperature influence on the dynamic binding capacity of a monolithic ion-exchange column. J Chromatogr A 987, 159-68.

Nuesch, J. P., Lacroix, J., Marchini, A. and Rommelaere, J., 2012. Molecular pathways: rodent parvoviruses—mechanisms of oncolysis and prospects for clinical cancer treatment. Clin Cancer Res 18, 3516-23.

Okada, T., Nonaka-Sarukawa, M., Uchibori, R., Kinoshita, K., Hayashita-Kinoh, H., Nitahara-Kasahara, Y., Takeda, S. and Ozawa, K., 2009. Scalable purification of adeno-associated virus serotype 1 (AAV1) and AAV8 vectors, using dual ion-exchange adsorptive membranes. Hum Gene Ther 20, 1013-21.

Paradiso, P. R., 1981. Infectious process of the parvovirus H-1: correlation of protein content, particle density, and viral infectivity. J Virol 39, 800-7.

Paradiso, P. R., Williams, K. R. and Costantino, R. L., 1984. Mapping of the amino terminus of the H-1 parvovirus major capsid protein. J Virol 52, 77-81.

Q6B. 1999. ICH HARMONISED TRIPARTITE GUIDELINE SPECIFICATIONS: TEST PROCEDURES AND ACCEPTANCE CRITERIA FOR BIOTECHNOLOGICAL/BIOLOGICAL PRODUCTS Q6B ICH Expert Working Group.

Qu, G., Bahr-Davidson, J., Prado, J., Tai, A., Cataniag, F., McDonnell, J., Zhou, J., Hauck, B., Luna, J., Sommer, J. M., Smith, P., Zhou, S., Colosi, P., High, K. A., Pierce, G. F. and Wright, J. F., 2007. Separation of adeno-associated virus type 2 empty particles from genome containing vectors by anion-exchange column chromatography. J Virol Methods 140, 183-92.

Rajamanickam, V., Herwig, C. and Spadiut, O., 2015. Monoliths in Bioprocess Technology. Chromatography, 195-212.

Rajendran, R., Lingala, R., Vuppu, S. K., Bandi, B. O., Manickam, E., Macherla, S. R., Dubois, S., Havelange, N. and Maithal, K., 2014. Assessment of packed bed bioreactor systems in the production of viral vaccines. AMB Express 4, 25.

Rommelaere, J., Geletneky, K., Angelova, A. L., Daeffler, L., Dinsart, C., Kiprianova, I., Schlehofer, J. R. and Raykov, Z., 2010. Oncolytic parvoviruses as cancer therapeutics. Cytokine & growth factor reviews 21, 185-95.

Tattersall, P. and Bratton, J., 1983. Reciprocal productive and restrictive virus-cell interactions of immunosuppressive and prototype strains of minute virus of mice. J Virol 46, 944-55.

Tattersall, P., Cawte, P. J., Shatkin, A. J. and Ward, D. C., 1976. Three structural polypeptides coded for by minite virus of mice, a parvovirus. J Virol 20, 273-89.

Toolan, H. W., Dalldore, G., Barclay, M., Chandra, S. and Moore, A. E., 1960. An Unidentified, Filtrable Agent Isolated from Transplanted Human Tumors. Proceedings of the National Academy of Sciences of the United States of America 46, 1256-8.

Tuynder, M., Fiucci, G., Prieur, S., Lespagnol, A., Géant, A., Beaucourt, S., Duflaut, D., Besse, S., Susini, L., Cavarelli, J., Moras, D., Amson, R., Telerman, A., 2004, Translationally controlled tumor protein is a target of tumor reversion, PNAS, Vol. 101, No. 43, pp. 15364-15369

Ungerechts, G., Bossow, S., Leuchs, B., Holm, P. S., Rommelaere, J., Coffey, M., Coffin, R., Bell, J. and Nettelbeck, D. M., 2016. Moving oncolytic viruses into the clinic: clinical-grade production, purification, and characterization of diverse oncolytic viruses. Mol Ther Methods Clin Dev 3, 16018.

Venkatakrishnan, B., Yarbrough, J., Domsic, J., Bennett, A., Bothner, B., Kozyreva, O. G., Samulski, R. J., Muzyczka, N., McKenna, R. and Agbandje-McKenna, M., 2013. Structure and dynamics of adeno-associated virus serotype 1 VP1-unique N-terminal domain and its role in capsid trafficking. J Virol 87, 4974-84.

Weaver, J., Husson, S. M., Murphy, L. and Wickramasinghe, S. R., 2013. Anion exchange membrane adsorbers for flow-through polishing steps: Part II. Virus, host cell protein, DNA clearance, and antibody recovery. Biotechnology and bioengineering 110, 500-10.

Weiss, N., Stroh-Dege, A., Rommelaere, J., Dinsart, C. and Salome, N., 2012. An in-frame deletion in the NS protein-coding sequence of parvovirus H-1PV efficiently stimulates export and infectivity of progeny virions. J Virol 86, 7554-64.

Willoughby, E. W. and Lambert, A., 1983. A sensitive silver stain for proteins in agarose gels. Anal Biochem 130, 353-8.

Wobus, C. E., Hugle-Dorr, B., Girod, A., Petersen, G., Hallek, M. and Kleinschmidt, J. A., 2000. Monoclonal antibodies against the adeno-associated virus type 2 (AAV-2) capsid: epitope mapping and identification of capsid domains involved in AAV-2-cell interaction and neutralization of AAV-2 infection. J Virol 74, 9281-93.

Xia, X. 2007. Protein Isoelectric Point, Bioinformatics and the Cell, Springer, US, pp. 207-219

Zolotukhin, S., Byrne, B. J., Mason, E., Zolotukhin, I., Potter, M., Chesnut, K., Summerford, C., Samulski, R. J. and Muzyczka, N., 1999. Recombinant adeno-associated virus purification using novel methods improves infectious titer and yield. Gene Ther 6, 973-85.

The invention claimed is:

1. A method for producing full active H-1 parvovirus particles, said method comprising:
   (a) providing the producer cell line NB-324K;
   (b) growing the cell line under suitable conditions and infecting the cells at a cell density from 2.0 to $5.0 \times 10^4$ cells/cm$^2$ with the H-1 parvovirus at a MOI of 0.5 to $2 \times 10^{-2}$ PFU/cells;
   (c) harvesting the cells 2 to 6 days post-infection and obtaining a cell pellet by centrifugation;
   (d) subjecting the resuspended cell pellet to a mechanical, physical or chemical cell lysis method for obtaining a H-1 parvovirus containing cell lysate;
   (e) sonicating the cell lysate and subjecting it to DNAse treatment;
   (f) clarifying the DNAse-treated parvovirus harvest by filtration; and
   (g) applying the filtrate of step (f) to an anion exchange column in about 0.15 M NaCl which leaves empty H-1 parvovirus particles and impurities in the flow through and full H-1 parvovirus particles on the column, and then eluting the full H-1 parvovirus particles with NaCl having a concentration of about 0.25-0.30 M;
   (h) concentrating and exchanging buffer of the eluate of step (g) through a desalting column or by tangential flow filtration; and
   (i) formulating in Iodixanol/Ringer solution.

2. The method of claim 1, wherein the cell density of step (b) is from 3.0 to $4.0 \times 10^4$ cells/cm$^2$.

3. The method of claim 1, wherein the filtration step (f) uses a 0.2 µm filter followed by a 0.1 µm filter.

4. The method of claim 1, wherein the anion exchange chromatography is DEAE column chromatography.

5. The method of claim 1, wherein in step (h) the desalting column is a cross-linked dextran for size exclusion chromatography.

6. The method of claim 1, wherein in step (h) the tangential flow filtration is made through a polyethersulfone membrane with 30 KDa cut off.

7. The method of claim 1, wherein the viral particles obtained in step (h) are in Ringer solution and are then mixed with 65.2% Iodixanol to 48% Iodixanol final concentration.

* * * * *